United States Patent [19]

Hosaka et al.

[11] 4,418,152
[45] Nov. 29, 1983

[54] IMMUNOLOGICAL, DIAGNOSTIC REAGENTS HAVING PARTICULATE CARRIERS OF GLYCIDYL ACRYLATE POLYMERS

[75] Inventors: Shuntaro Hosaka; Yasuo Murao; Yasuro Kawabata, all of Kamakura, Japan

[73] Assignee: Toray Industries, Inc., Tokyo, Japan

[21] Appl. No.: 250,073

[22] Filed: Apr. 1, 1981

[30] Foreign Application Priority Data

Apr. 4, 1980 [JP] Japan ................... 55-43618

[51] Int. Cl.$^3$ .................. G01N 33/54; G01N 33/76
[52] U.S. Cl. .................. 436/511; 436/513; 436/531; 436/533; 436/534; 436/818; 436/828
[58] Field of Search ............... 23/230 B; 424/12; 436/534, 511, 513, 531, 533, 534, 818, 828

[56] References Cited

U.S. PATENT DOCUMENTS 4,292,038 9/1981 Kondo .................. 23/230 B

FOREIGN PATENT DOCUMENTS 38960 11/1981 European Pat. Off. .

OTHER PUBLICATIONS

R. S. Molday et al., Nature, vol. 249, pp. 81–82 (May 3, 1974).
Chemical Abstracts, 96:82306y (1982).

Primary Examiner—Sidney Marantz
Attorney, Agent, or Firm—Austin R. Miller

[57] ABSTRACT

A diagnostic reagent for immunological tests for detecting or measuring a component in human or animal body fluids or for labeling cells, including immunochemicals immobilized on a particulate carrier characterized in that fine particles having an average diameter in the range of about 0.03 to about 10 μm and comprising a cross-linked polymer having a repeating unit represented by the general formula

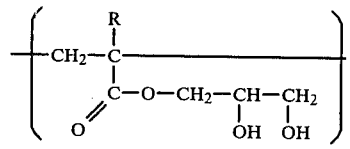

wherein R stands for hydrogen or a methyl group, are used as the particulate carrier.

8 Claims, No Drawings

IMMUNOLOGICAL, DIAGNOSTIC REAGENTS HAVING PARTICULATE CARRIERS OF GLYCIDYL ACRYLATE POLYMERS

BACKGROUND OF THE INVENTION

Field of the Invention

The present invention relates to diagnostic reagents for immunological tests. In particular, the invention relates to an improvement in or relating to a particulate carrier and diagnostic reagents for immunological tests for detecting or measuring a component in human or animal body fluids or for labeling cells, and especially relates to immunoparticles prepared by immobilizing immunochemicals on a particulate carrier.

In immunologically detecting or quantitatively analyzing either an antigen or antibody using the reaction between the antigen and antibody, an important method in immunological tests in clinical laboratories is the method of immobilizing a substance which reacts with a second substance to be detected, on a particulate carrier and carrying out a high sensitivity measurement utilizing the phenomenon of agglutination of said immobilized substance-carrier combination particles in the presence of the substance to be detected. Another method which has also been broadly used in clinical laboratory tests is the method of immobilizing a substance to be detected on a particulate carrier, utilizing the fact that agglutination, of particles immobilizing the substance to be detected due to the presence of an antigen or antibody specifically reacting with the substance to be detected, is inhibited by the presence of the substance to be measured in the body fluids, thereby detecting or quantitatively analyzing the substance to be detected. The latter method is often called the agglutination inhibition method. In addition, cell labeling has been frequently used for immunological testing. Cell labeling is the method of immobilizing a substance, which selectively binds to specific cells, on a particulate carrier and labeling the cells by determining whether or not the particles bind to the cells.

Such immobilized substance-particulate carrier combinations are referred to as "immunoparticles".

As a particulate carrier as a part of a diagnostic reagent for immunological tests using such immunoparticles for agglutination reaction, substances used include red corpuscles of mammals, including man and birds, particles of an inorganic substance such as kaolin and carbon, and latex of organic high polymers such as natural rubber latex and polystyrene latex. Of these, red corpuscles can immobilize many kinds of antigens and antibodies and the applicable range thereof is the broadest. However, red corpuscles have disadvantages in that there are differences in quality depending upon the individual animals from which it is selected. Red corpuscles are also difficult to store and they may be non-specifically agglutinated by human serum.

The most widely used non-organism originating carrier particles are polystyrene particles. Polystyrene is stable and because it is a synthetic polymer, the quality can be controlled. Because polystyrene is hydrophobic and has properties of adsorbing various proteins, immobilization of an antigen or antibody on polystyrene is usually carried out by physical adsorption. When an antigen or antibody is immobilized by physical adsorption, an euilibrium may occur between the immobilized antigen (or antibody) and a free antigen (or antibody) and result in a competitive reaction which takes place between the antigen (or antibody) immobilized on particles and the free antigen (or antibody) toward a corresponding antibody (or antigen) which is an objective substance of the measurement. This competitive reaction works to inhibit agglutination. As a result, insufficient sensitivity and stability occurs in many instances. Moreover, when the protein component in the body fluids of an object of detection is adsorbed by the polystyrene, agglutination takes place even when the objective reaction between the antigen and the antibody does not take place and a biological false-positive reading results. Also, substances incapable of being physically adsorbed to polystyrene cannot be immobilized by this method. Because of these disadvantages, polystyrene particles are used practically only within a limited range.

In order to overcome these difficulties, it has been proposed to use other reagents bonding an antigen or antibody to a carrier by covalent bonding. Reagents which bond human chorionic gonadtropin to a styrene—methacrylic acid copolymer latex using carbodiimide (DT No. 2,649,218), reagents consisting of particles having diameters of 0.01–0.9 microns bonding human chorionic gonadtropin, human serum albumin or aggregated γ-globulin to various latices via amide bond such as carboxylated styrene—butadiene copolymer, carboxylated polystyrene, carboxylated polystyrene having an amino group, acrylic acid polymer, acrylonitrile polymer, methacrylic acid polymer, acrylonitrile-butadiene-styrene terpolymer, polyvinyl acetate acrylate, polyvinyl pyridine and vinyl chloride—acrylate copolymer (Japanese Patent Application Publication No. 12966/1978) and reagents obtained by copolymerizing methyl methacrylate, 2-hydroxyethyl methacrylate and methacrylic acid and bonding treponema antigen to a latex of the copolymer containing hydroxyl group and carboxyl group prepared by the copolymerization by cyanogen bromide or carbodiimide method ("The Japanese Journal of Clinical Pathology", 27, Supplementary Edition, page 422 (1978), have been proposed.

Where many of the aforementioned carriers contain a large amount of hydrophobic portions in the main component of the polymer, for example, the styrene-methacrylic acid copolymer, they tend to adsorb protein, especially with blood plasma and serum where high concentrations of protein occur. When protein is adsorbed onto a carrier from the test body fluids, it may interfere with the objective reaction of the antigen and the antibody, causing a reduction in the selectivity or sensitivity of the agglutination reaction.

Some of the aforementioned carriers, for example, the acrylic acid polymer, are electrolytes. It is generally known that the existence of an electrolyte in a large amount weakens the binding of the antigen to the antibody. Further, an acrylic acid polymer and a methacrylic acid polymer ionizingly bond to protein high in isoelectric point pH. As mentioned above, it is disadvantageous to have protein other than the constitutional element of the objective immunological reaction nonselectively attached to the carrier. Accordingly, it is disadvantageous to use a polymer consisting mainly of an electrolyte as the carrier of a reagent for an agglutination reaction.

OBJECTS OF THE INVENTION

The principal object of the present invention is to provide carriers for diagnostic reagents for immunological tests which make it possible to immobilize immunochemicals by chemical bonding, which are stable and unlikely to agglutinate non-specifically by test body fluid and which are free from non-specific adsorption of protein in the test body fluid and non-specific adhesion to cells.

DESCRIPTION OF THE INVENTION

The present invention provides diagnostic reagents, for immunological tests, including immunochemicals immobilized on a particulate carrier, characterized in that fine particles having an average diameter of 0.03–10 μm and comprising a cross-linked polymer having a repeating unit represented by the general formula

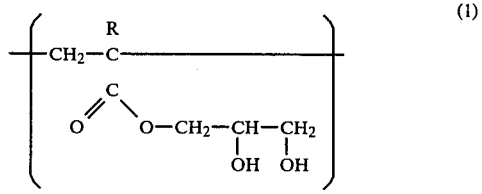

(wherein R stands for hydrogen or a methyl group) are used as the particulate carrier.

The particulate carrier, according to the present invention, may be prepared by polymerizing a mixture of addition polymerizable monomers containing not less than 50 mol % of glycidyl acrylate and/or glycidyl methacrylate in a medium in which the mixture of monomers is soluble but in which the produced polymer is not soluble, opening the ring of an epoxy group in the produced polymer by hydrolysis to thereby convert said epoxy group to $\alpha,\beta$-diol.

The polymer is cross-linked to an extent of showing substantial insolubility. Where a copolymerizable monomer co-exists in the polymerization system, it is preferable that the amount thereof be less than 50 mol %. Copolymerizable monomers which can be used include, but are not limited to, 2-hydroxyethyl acrylate, 2-hydroxyethyl methacrylate, the methacrylic acid ester of polyethyleneglycol monoalkylether having a degree of polymerization within the range of 2–25, acrylamide, methacrylamide, N-vinylpyrrolidone and vinyl acetate.

Where glycidyl acrylate and/or glycidyl methacrylate are polymerized, a small amount of a polyfunctional monomer containing two or more carbon-carbon double bonds within the molecule contained in the monomer, and by a side reaction during the polymerization, a cross-linked structure is formed in the polymer produced which becomes insoluble. Addition of a cross-linking agent to the polymerization system is not indispensable, but it is normally desirable to add a polyfunctional monomer containing two or more polymerizable carbon-carbon double bonds inside the molecule upon polymerization to positively cross-link the polymer. There are many polyfunctional monomers suitable for addition to the polymerization system for such purpose. Examples of such polyfunctional monomers include, but are not limited to, divinyl benzene, ethyleneglycol dimethacrylate, diethyleneglycol dimethacrylate, triethyleneglycol dimethacrylate, N,N'-methylenebisacrylamide, divinyl succinate, diallyl succinate, vinyl methacrylate, allyl methacrylate, triallyl cyanurate and triallyl isocyanurate. The amount of the cross-linking agent to be added is generally not more than 30 mol % of the total monomers.

The cross-linking may also be carried out on the produced polymer by utilizing the reactivity of the produced polymer after the polymerization reaction by reacting the produced polymer with a polyfunctional compound. For example, after polymerizing glycidyl acrylate and/or glycidyl methacrylate, the polymer may be cross-linked by reacting an epoxy group contained in the produced polymer with a diamine such as ethylene diamine. An unsaturated carboxylic acid such as acrylic acid, methacrylic acid, maleic acid, fumaric acid or maleic anhydride, may be added as a copolymerization component to the polymerization system to thereby utilize a carboxylic group originated therein as a functional group for immobilizing immunochemicals. It is preferable to limit the amount of such an electrolytic monomer to not more than 30 mol % of the total monomers.

The polymerization reaction is carried out by emulsion polymerization, suspension polymerization, or precipitation polymerization. Any of these polymerization methods is suitable for the purpose of this invention because the polymer is produced as particles during the polymerization reaction. Precipitation polymerization is a method of carrying out polymerization in a medium in which the monomer or monomers are soluble, but in which the polymer produced is not soluble. In using this method, the average diameter of the polymer particles produced may be controlled. By selecting the proper combination of the monomer or monomers with the polymerization medium, polymer particles may be produced with an average diameter within the range of 0.03–10 μm. In this type of polymerization, distribution of the particle diameters is relatively narrow. With precipitation polymerization, unlike emulsion polymerization and suspension polymerization, neither an emulsifier nor a suspension stabilizer are required and these additives do not have to be removed after the polymerization reaction. Precipitation polymerization is the preferred method of polymerization when the total amount of glycidyl acrylate and glycidyl methacrylate are not less than 50 mol % of the total monomers.

Suitable polymerization media include, but are not limited to, ethyl acetate, n-propyl acetate, isopropyl acetate, butyl acetate and their isomers, and the propionic acid esters corresponding to the foregoing, ketones such as methylethyl ketone, methyl n-propyl ketone, methyl isopropyl ketone, methylbutyl ketone and their isomers as well as benzene, toluene, o-xylene, m-xylene, p-xylene, carbon tetrachloride, chloroform and bromoform. Mixtures of these compounds may also be used as the polymerization media.

As the polymerization initiator, ordinary radical polymerization initiators may be used including, but not limited to, azo compounds such as 2,2'-azobisisobutyronitrile, 2,2'-azobis (2,4-dimethylvaleronitrile) and 2,2'-azobis (2,4-dimethyl-4-methoxyvaleronitrile) and peroxides such as benzoyl peroxide, dilauryl peroxide and ditertiarybutyl peroxide.

The polymerization temperature may be within the temperature range of an ordinary radical polymerization. The range of 20°–80° C. is especially preferred.

The concentration of the polymerization initiator in the polymerization mixture of the present invention is about 0.001–0.03 mol/liter. The concentration of the monomer in the polymerization mixture is preferably within the range of about about 5–50% by weight. When the concentration of the monomer exceeds 50% by weight, the particles of the polymer tend to aggregate. When the concentration of the monomer is less than 5% by weight, the present invention may be practiced, but the yield of fine particles of polymer becomes small and productivity decreases. It is preferable to carry out the polymerization after replacing the air with an inert gas such as nitrogen or argon.

After glycidyl acrylate and/or methacrylate is polymerized with or without another copolymerizable monomer, the epoxy group in the polymer produced is converted to $\alpha,\beta$ diol by hydrolysis. The epoxy group is preferably hydrolyzed by an acid or alkali. For such acid, an aqueous solution of a strong acid is preferred. Such acids would include, but are not limited to, sulfuric acid, hydrochloric acid, nitric acid, phosphoric acid, benzene sulfonic acid and toluene sulfonic acid. An acid concentration within the range of about 0.01–2 N is preferred. A hydrolysis temperature within the range of about 0°–50° C. is preferred. The hydrolysis reaction may be accelerated by adding an organic solvent miscible with water, having the ability to swell the polymer, such as acetone, tetrahydrofuran, dioxane and dimethyl sulfoxide. It is thought that because the polymer swells by these solvents, diffusion of the acid to the inside of the polymer particles is accelerated and as a result, the reaction time for hydrolysis is reduced.

As an alkali for hydrolysis, an aqueous solution of sodium hydroxide and potassium hydroxide may be used in the same manner as the aqueous solution of the strong acid.

By treating the particulate polymer before or after the treatment with such acid or alkali, with ammonia, hydrazine or an organic amine having not less than 2 amino groups in the molecule, an amino group may be introduced into the particulate polymer. As a result, it is possible to obtain a particulate polymer having a repeating unit represented by the general formula (1) and having an amino group.

Organic amines having not less than 2 amino groups in the molecule which may be added would include, but not be limited to, aliphatic diamine such as ethylenediamine, propylenediamine, butylenediamine, pentamethylenediamine and hexamethylenediamine, and those containing another functional group such as lysine. The amino group introduced into the polymer may be utilized as a functional group for immobilizing immunochemicals as will be described later herein.

The shape of the particles produced is spherical in many cases. However, being spherical is not a necessary condition and the shape may be irregular. The diameter of an irregularly shaped particle is defined as ½ of the sum of the largest diameter and the smallest diameter. The average diameter is expressed by d defined by formula (2)

$$\bar{d} = \sum_{i=1}^{N} d_i / N \quad (2)$$

wherein $D_i$ is the diameter of number i particle and N is a total number of particles. The particle size where the agglutination reaction is easily observable is that particle size where the average diameter ranges from about 0.2 μm to 10 μm. For the purpose of labeling cells, particles whose average diameter ranges from about 0.03 μm to 5 μm are preferred. Particles either properly colored with a dye or pigment or imparted with fluroscence may be used for either an agglutination reaction or for labeling the cell.

The immobilization of immunochemicals on particles is preferably carried out by covalent bonding. The term "immunochemicals" means a component which is an object of measurement in body fluids, or a substance specifically bonding to cells. Known immunochemicals may be properly selected in accordance with the object of the tests. Immunochemicals are normally protein or contain a proper protein as a constituent component. Therefore, they may be immobilized on a particulate carrier of the present invention by a known method of immobilizing protein. For example, when the fine particulate carrier of the present invention contains hydroxyl groups in the molecule, by activating the carrier with cyanogen bromide and reacting the activated carrier with proteins, the protein may be immobilized on the carrier. When carboxyl groups are introduced into the polymer by copolymerization, an amide bond from that carboxyl group may be formed with an amino group of protein and thereby immobilize the immunochemicals.

The amide bond from the carboxyl group of the polymer and the amino group of the immunochemical may be formed in one stage by reacting the two groups in the presence of carbodiimide as a condensing agent. However, in order to minimize the deactivation of the immunochemicals, it is recommended that a method of condensing the carboxy group of the polymer with N-hydroxysuccinimide and reacting the produced active ester with the immunochemicals having an amino group be used. Immunochemicals may be immobilized on the polymer carrier to which an amino group introduced by the aforesaid method utilizing the reactivity of an amino group by a known method. Where immunochemicals contain an amino group, a method of immobilizing the immunochemicals on a carrier in the presence of a compound having not less than two functional groups bondable to an amino group in the molecule used as a binder is preferred. Preferred binders include, but are not limited to, aliphatic, $\alpha,\omega$-dialdehyde such as succinaldehyde, glutaraldehyde and aldipaldehyde and polymeric aldehydes such as polyacrolein, dialdehyde starch and dialdehyde dextran. In immobilizing immunochemicals, when a fine particulate polymer containing an amino group is treated with a binder, the fine particulate polymer is washed to remove any free binder so that when the resulting fine particulate polymer is brought into contact with the immunochemical, the reduction of the activity of the immunochemical is minimized. With this method, when immunochemicals are immobilized on a fine particulate carrier with a binder, the bond formed is strong and the immobilized immunochemicals are not released from the fine particulate carrier. To further strengthen the bond where necessary, the immobilized immunochemicals may be treated with sodium borohydride or sodium cyanoborohydride or dimethylamine borone.

Futher, when immobilizing immunochemicals on a fine particulate carrier, it may be effective to immobilize the immunochemical by means of a so-called spacer on the carrier. For example, when there is a carboxyl group as a functional group on the fine particulate polymer, immobilizing immunochemicals by means of a spacer such as ξ-aminocaproic acid and hexamethylenediamine is preferred.

Methods of immobilizing immunochemicals on a fine particulate carrier are not limited to the aforementioned examples and it is possible to empirically select methods of immobilizing immunochemicals that are high in degree of retention of the immunological activity in accordance with the individual cases of immunochemicals to be immobilized.

Immunochemicals for immobilization on fine particles may be selected from well-known immunochemicals such as, but not limited to, treponemal antigen, hepatitis B surface antigen (HBs antigen), anti-HBs antigen antibody, rubella viral antigen, toxoplasma antigen, streptolysin O, antistreptolysin O antibody, mycoplasma antigen, human chorionic gonadtropin (HCG), anti-HCG antibody, aggregated human IgG, nuclear protein, DNA, rheumatoid factor, anti-C reactive protein (CRP) antibody, estrogen, anti-estrogen antibody, anti-human C1q antibody, anti-C1r antibody, anti-C1s antigen, anti-C2 antibody, anti-C3 antibody, anti-C4 antibody, protein A, anti-human IgM antibody, anti-human IgG antibody, anti-human IgA antibody, IgG and IgM in accordance with the test objects.

The fine particulate carrier constituting the diagnostic reagent for immunological tests of the present invention is characterized in that it is stable to test body fluids; it is unlikely to be agglutinated non-specifically by such fluids; it does not non-specifically adsorb protein of the test body fluids; it may be used successfully for detecting or measuring an immunological reaction by agglutination of particles; it is free from non-specific adhesion to cells; and it may be successfully used in labeling cells.

The present invention is further described by, but not limited to, the examples which follow.

EXAMPLE 1

(Preparation of carrier fine particles)

Glycidyl methacrylate, 2-hydroxyethyl methacrylate and ethyleneglycol dimethacrylate were mixed at a molar ratio of 85.7:9.5:4.8. 24 parts by weight of the resultant mixture of monomers was dissolved in 76 parts of ethyl propionate and 0.13 parts of 2,2′-azobis(2,4-dimethyl-4-methoxyvaleronitrile) was added to the resultant solution and the mixture was polymerized. The initial concentration of the polymerization initiator was 4.7 mmol/liter. The polymerization was carried out in an argon atmosphere at 40° C. for 3 hours without agitation. After lapse of a predetermined period, an opaque polymerization mixture was poured into acetone and centrifuged at 1500 g for 10 minutes. The precipitated particles were dispersed again with methanol, washed and then centrifuged again. By drying under a reduced pressure, 11.3 parts of a fine particulate were obtained. One part of this fine particulate polymer was dispersed in a mixed solution of 50 parts of water, 50 parts of acetone and 0.2 parts of concentrated sulfuric acid, and stirred at 30° C. for 7 days to carry out hydrolysis. An optical microscopic photograph (1,000 times in magnification) of the fine polymer particles was taken and the distribution of the particle diameters was measured as shown in Table 1. The average diameter was 3.52 μm and the standard deviation was 0.447 μm. Thus, the ratio of the standard deviation/average diameter was 0.126.

TABLE 1

| Particle diameter (μm) | Frequency (%) |
|---|---|
| 1.70–1.90 | 0.7 |
| 1.90–2.10 | 0.7 |
| 2.10–2.30 | 1.4 |
| 2.30–2.50 | 1.4 |
| 2.50–2.70 | 0.7 |
| 2.70–2.90 | 2.1 |
| 2.90–3.10 | 7.8 |
| 3.10–3.30 | 8.5 |
| 3.30–3.50 | 12.1 |
| 3.50–3.70 | 24.3 |
| 3.70–3.90 | 29.3 |
| 3.90–4.10 | 7.1 |
| 4.10–4.30 | 2.8 |
| 4.30–4.50 | 0.7 |

After the hydrolyzed fine particles were dried under reduced pressure, 0.1 g of the dried fine particles were dispersed in 10 ml of ethylenediamine and stirred at 80° C. for 4 hours. After completion of the reaction, the fine particles were centrifuged and washed with distilled water. The particles contained an amino group and were capable of immobilizing immunoprotein by the method described below.

(Immobilization of anti-human IgG antibody)

The aforesaid fine particles containing amino groups were dispersed in 20 ml of distilled water with the polymer content 0.5% and the resultant aqueous dispersion was mixed with 1 ml of a 25% aqueous solution of glutaraldehyde. The resultant mixed solution was stirred at 30° C. for 1 hour. Thereafter it was repeatedly centrifuged and then the precipitated particles were washed with distilled water. After washing with distilled water 4 times, the particles activated by the glutaraldehyde were dispersed in 1.5 ml of a phosphate buffered physiological saline solution (isotonic sodium chloride solution) (hereinafter referred to as PBS) wherein the concentration of a mixture of disodium hydrogen phosphate+potassium hydrogen phosphate was 0.01 mol/liter, the concentration of sodium chloride was 0.14 mol/liter and the pH was 7.2. To the resulting dispersion was added 0.5 ml of a liquid obtained by diluting an IgG fraction solution of anti-human IgG anti-serum (rabbit) (antibody 1.9 mg/ml) 10 times with PBS. The resulting dispersion was stirred at 30° C. for 3 hours and thereafter allowed to stand without agitation at room temperature for 16 hours. The particles were then subjected to centrifugal sedimentation with PBS 4 times and washed. The washed particles were dispersed in 2 ml PBS and to the resultant dispersion was added 20 mg of bovine serum albumin (hereinafter referred to as BSA) and the obtained dispersion was stored at 4° C.

The activity of particles immobilizing the anti-human IgG antibody prepared in the manner described above was measured by the microplate method. That is, 100 μl of PBS solution of the predetermined concentration of human IgG was placed at each well (V-shaped) of a microplate to which was added 10 μl of a dispersion of particles immobilizing the anti-human IgG antibody. The resultant dispersion was shaken and mixed and, thereafter, allowed to stand at room temperature for 2 hours. The degree of agglutination was determined by visual observation of the sedimentation pattern. The results are as shown in Table 2. As can be seen, agglutination took place when the concentration of human IgG was at least 0.01 μg/ml. Whereas, after 100 μl of the solution of the same concentration of human IgG was placed in each well of the microplate, 10 μl of anti-human IgG anti-serum (rabbit), having a concentration of the antibody of 1 mg/ml was added to the solution, the resultant solution was incubated at room temperature for 2 hours. Thereafter, 10 μl of a dispersion of fine particles immobilizing anti-human IgG antibody was added thereto and then the same procedure was taken as previously described. A sedimentation pattern was observed as above and no agglutination was observed in any one of the wells. Thus, it was confirmed that agglutination, as shown in Table 2, was caused by the reaction between the antigen and the antibody and that the agglutination could be detected when the concentration of human IgG was between 0.01 μg/ml and 1 μg/ml.

TABLE 2

| Concentration of human IgG (μg/ml) | Agglutination* |
|---|---|
| 100 | − |
| 10 | − |
| 1 | +++ |
| 0.1 | +++ |
| 0.01 | ++ |
| PBS | − |

*− State wherein the particles gather around the center of the wells, sinking to form small circles and there are no particles at the peripheries of the wells that are in transparent states.
+ State wherein small circles around the centers become somewhat smaller than in the case of − and agglutinated particles sink a little at the peripheries that become somewhat opaque.
++ State wherein small circles around the centers become very small and the peripheries become opaque.
+++ State wherein small circles around the centers disappear, agglutinated particles sink uniformily and the entirety becomes opaque like a uniform film.

EXAMPLE 2

(Immobilization of human IgG)

To amino group-containing fine particles prepared in the same manner as in Example 1, human IgG was immobilized instead of the anti-human IgG antibody used in Example 1. The particles were treated with ethylenediamine. Water-containing fine particles, rather than dry particles, separated by centrifugal sedimentation, were used. The amount of a 25% aqueous solution of glutaraldehyde used was not 1 ml, but 3 ml. Except for these modifications, the same procedure as Example 1 was repeated. The fine particles were dispersed such that 0.6 g of the polymer was contained in 2 ml of PBS. The dispersion was mixed with 1 ml of a PBS solution of human IgG having a concentration of 0.8 mg/ml and the resultant mixture was stirred at 30° C. for 14 hours. After the reaction, the particles were subjected to centrifugal sedimentation, washed and thereafter, the particles were dispersed in 2 ml of PBS containing 0.4 mg of sodium azide and 20 mg of BSA and the resultant dispersion was stored at 4° C. The aforesaid dispersion was reacted, by the microplate method, in the same manner as in Example 1, with an IgG fraction of anti-human IgG antiserum (rabbit) to carry out an agglutination test. The results are as shown in Table 3. Where a similar microplate test was carried out using an IgG fraction of normal rabbit serum instead of the fraction of anti-human IgG antiserum (rabbit), agglutination was not observed. Accordingly, an agglutination reaction is specific, and caused by the reaction between an antigen and an antibody.

TABLE 3

| Concentration of anti-human IgG antibody (μg/ml) | Agglutination |
|---|---|
| 100 | +++ |
| 10 | +++ |
| 1 | +++ |
| 0.1 | +++ |
| 0.01 | +++ |
| 0.001 | + |
| PBS | − |

The detection limit of anti-human IgG antibody by this fine particle method is about 1 ng/ml, a detection sensitivity matching that of radioimmunoassay.

As another method of testing agglutination, 10 μl each of a solution of anti-human IgG antibody and a dispersion of IgG-immobilized particles, both having predetermined concentrations, are mixed. The agglutination of the mixture may be observed with the naked eye after 3 minutes. By this method, it was possible to detect anti-human IgG antibody having a concentration of not less than 1 μg/ml.

EXAMPLE 3

(Preparation of a fine particulate carrier)

Polymerization was carried out in the same manner as in Example 1 to obtain fine polymer particles. The fine polymer particles were dispersed in a 10% aqueous solution of ammonia with the polymer content 0.66% and the dispersion was stirred at 30° C. for 2 hours to effect amination. After washing the aminated particles with distilled water, they were dispersed in a 0.3% aqueous solution of sulfuric acid (water:acetone=1:1 by volume) with the polymer content 1% and the dispersion was stirred at 30° C. for 10 days to carry out hydrolysis. After the completion of hydrolysis, the particles were thoroughly washed with distilled water.

(Immobilization of TP antigen)

The amino group-containing fine carrier particles prepared as described above, were dispersed in a 3.3% aqueous solution of glutaraldehyde with the polymer content 0.5% and the dispersion was stirred at 30° C. for 1 hour. The particles activated by glutaraldehyde were sufficiently washed with distilled water and thereafter reacted with the cell componenet of Treponema pallidum (herinafter referred to as TP) Nichols strain, as described hereinbelow. While a dispersion obtained by dispersing TP cells in PBS at a ratio of $10^9$/ml was being cooled with ice water, it was treated with 10 KHz ultrasonic wave for 20 minutes to destroy the cells to produce an original solution of TP antigen. One part by volume of a PBS dispersion of said particles activated with glutaraldehyde (polymer content 5%) was mixed with 1 part by volume of the original solution of TP antigen and the resultant mixture was stirred at 30° C. for 3 hours. After completion of the reaction, the particles immobilizing TP antigen were sufficiently washed with distilled water and dispersed in PBS to which was added 1% of BSA and 0.02% of sodium azide to result in a dispersion with a polymer content of 2.5%. This particle immobilizing TP antigen and syphilis positive serum having a titer of 1280 according to the method of TPHA were reacted on a microplate the same as in Example 1 and Example 2. The serum specimen was diluted serially to $2^n$ times starting from 80 times with an absorbing diluent of a commercially available TPHA kit (manufactured by Fujizoki Pharmaceutical Co. of Japan). As a control, a similar test was carried out with respect to negative serum. With the positive serum, agglutination was visually observed at up to 10,240 times dilution, whereas in the case of the negative serum, no agglutination was visually observed at any dilution ratio. In another test, wherein 10 μl each of a dispersion of particles immobilizing TP antigen and the diluted serum specimen were mixed on a glass plate and evaluated after 3 minutes, agglutination, where the aforesaid positive serum was diluted to up to 40 times, was observed. With the negative serum, no agglutination was observed when it was diluted more than 2 times.

EXAMPLE 4

(Dyeing of fine particulate carrier)

To 5 ml of a dispersion of fine carrier particles (polymer content 1%) prepared by the method described in Example 3 was added 0.6 ml of an aqueous solution of toluidine blue 0, exhibiting an absorbance of 0.48 at 635 nm when diluted to 200 times. The resultant mixed solution was stirred at 30° C. for 30 minutes and thereafter washed with PBS. The particles were dyed blue and little elution of the dye used was observed.

(Immobilization of TP antigen)

The aforementioned dyed particles were activated with glutaraldehyde in the same manner as in Example 3. The original solution of TP antigen was diluted 4 times with PBS containing BSA at a concentration of 0.5 mg/ml. One part by volume of the diluted TP antigen solution and 1 part by volume of a dispersion of the dyed particles activated with glutaraldehyde (polymer content 2.5%) were mixed and stirred at 30° C. for 2 hours. After completion of the reaction, the fine particles immobilizing TP antigen were washed with PBS and thereafter dispersed in PBS containing 1% of BSA and 0.02% of sodium azide at such a ratio as to make the polymer content 0.25% and stored at 4° C.

The verification of the activity of the dyed particles immobilizing TP antigen was carried out as follows. 50 μl each of the diluted serum specimen (for dilution, an absorbing diluent the same as that in Example 3 was used) and a dispersion of the dyed particles immobilizing TP antigen were placed in each well (U-shaped) of a microplate and were mixed. The mixture was allowed to stand still for 2 hours and thereafter, a sedimentation pattern was examined with the naked eye. The TPHA titer of the positive serum used for this test was 1280. As a result of making serial dilution to $2^n$ times starting from 20 times, agglutination was observed when the dilution ratio was not more than 5,120. Herein, the dilution ratios mean the dilution ratios of serum after dilution with an absorbing diluent and mixing with a dispersion of the particles. As a control, using the negative serum, a similar experiment was carried out. As a result, agglutination was not observed when the dilution ratio exceeded 40.

EXAMPLE 5

(Immobilization of human chorionic gonadtropin)

Fine particles containing amino groups, prepared by the method described in Example 3, were activated with glutaraldehyde in the same manner as in Example 3. The particles activated with glutaraldehyde were dispersed in PBS with the polymer content adjusted to 1%. Human chlorionic gonadtropin having a purity of 3,230 IU/mg (hereinafter referred to as HCG) was dissolved in PBS at a concentration of 1 mg/ml. A dispersion of the particles activated with glutaraldehyde and an HCG solution were mixed at a volume ratio of 1:1 and the mixture was stirred at 30° C. for 16 hours. After completion of the reaction, the particles immobilizing HCG were washed with PBS and dispersed in PBS containing 1% of BSA at a ratio with polymer content adjusted to 2%. The verification of the activity of the particles immobilizing HCG was carried out in the following manner.

In each well of a U-shaped microplate, 100 μl each of an HCG/PBS solution having a predetermined concentration and anti-HCG antiserum (rabbit) solution having a predetermined concentration (both the anti-HCG antiserum and a liquid for dilution thereof employed herein were those of a commercially available kit for measuring a very small amount of HCG or LH, "Luteonosticon") were mixed and allowed to stand still at 23° C. for 2 hours for incubation. After the incubation, 10 μl of a dispersion of particles immobilizing HCG was added to each well, shaken and well mixed and thereafter allowed to stand still for 2 hours. The test results are in Table 4. To detect a very small amount of HCG, the anti-HCG antiserum used herein was diluted 5 times. It was then possible to detect HCG having a concentration of 10 IU/liter.

TABLE 4

| Verification of the activity of particles immobilizing HCG* | | | |
|---|---|---|---|
| Concentration of HCG (IU/liter) | Dilution ratio of anti-HCG antiserum | | |
| | 1 | 5 | 10 |
| 100 | +++ | − | − |
| 50 | +++ | − | − |
| 25 | +++ | ± | − |
| 10 | +++ | + | − |
| 5 | +++ | ++ | − |
| 1 | +++ | ++ | − |
| 0 | +++ | ++ | − |

*− A small clear-cut ring at the center of the bottom
± A ring somewhat larger than the negative pattern
+ A ring whose size is between /+ and ±
+ + Small film-like (ring forming) sedimentation
+ + + Film-like sedimentation throughout the bottom. All data visually observed.

EXAMPLE 6

(Preparation of a carboxyl group-containing fine particular carrier)

Glycidyl methacrylate, methacrylic acid, 2-hydroxyethyl methacrylate and ethyleneglycol dimethacrylate were mixed at a molar ratio of 75.7:10.0:9.5:4.8 24 parts of the mixture of monomers were dissolved in 76 parts of ethyl propionate and to the resultant solution was added 0.13 part of 2,2'-azobis (2,4-dimethyl-4-methyoxylvaleronitrile) and the resultant mixture was polymerized in an argon atmosphere at 40° C. for 2 hours. The opaque polymerization mixture obtained was treated in the same manner as in Example 1 to obtain 3.2 parts of fine polymer particles. The fine polymer particles thus obtained were hydrolyzed under the same conditions as in Example 1. The average diameter of the hydrolyzed particles in water was 0.5 μm. 100 mg of the hydrolyzed particles were dispersed in 4 ml of a 0.1 mol/liter solution of sodium chloride and when the pH was adjusted to 6.5 with a solution of disodium phosphate and monopotassium phosphate, the amount of the solution became 5 ml. 2.5 ml of this dispersion of carboxyl group-containing fine particles was cooled to 4° C., to which were added 1 mg of ε-aminocaproic acid and 10 mg of N-acetyl-N'-(3-dimethylamino propyl)-carbodiimide hydrochloride and the resultant mixture was stirred for 2 hours in an ice bath. Next, the same amount of a M/10 glycin—sodium hydrogen carbonate buffer solution (pH 7.0) was added to the aforesaid mixture. The obtained mixture was continuously stirred for 15 minutes and thereafter the particles were centrifuged and washed with water. One hundred mg of fine particulate carrier with a spacer were dispered in 2.5 ml of an aqueous solution of M/10 sodium chloride and while the resultant dispersion was being cooled in an ice bath, 2 mg of human IgG was added thereto. The pH of the dispersion at this time was 6.5. To this dispersion was added 10 mg of N-acetyl-N'-(3-dimethylaminopropyl)-carbodiimide hydrochloride and the resultant mixture was stirred in an ice bath for 2 hours. Next, the same amount of a glycin—sodium hydrogen carbonate buffer solution as described above was added thereto and the resultant mixture was continuously stirred for 15 minutes. Thereafter, the particles were centrifuged, washed with water and dispersed in 1 ml of PBS. On a glass plate, 10 μl each of the so-prepared dispersion of the particle immobilizing human IgG and a PBS solution of an IgG fraction of anti-human IgG antiserum (rabbit) were mixed and observed. When the concentration of anti-human IgG antiboy was 100 μg/ml, vigorous agglutination took place. However, when the concentration was 10 μg/ml, little agglutination was observed. As a result of carrying out a test according to the microplate method as in Example 2, agglutination was observed when the concentration of anti-human IgG antibody was at least 0.1 μg/ml.

EXAMPLE 7

Polymerization and hydrolysis were carried out under the conditions described in Example 1 and the fine polymer particles obtained were used as a carrier. One hundred mg of the fine carrier particles were dispersed in a 2 M aqueous solution of sodium carbonate (pH 11.0). Separately, a solution containing 100 mg of cyanogen bromide in 1.2 ml of N-methyl pyrrolidone was prepared. While the solution was being cooled in an ice bath, it was added to the aforementioned dispersion of the carrier particles. After stirring the resultant dispersion for 10 minutes on an ice bath, it was centrifuged and the activated particles were washed with a M/8 aqueous solution of hydrogen carbonate (pH 8.2). The operations of centrifuging and washing were repeated 3 times. Human IgG was dissolved in a M/8 aqueous solution of sodium hydrogen carbonate at a concentration of 1 mg/ml; 10 ml of the resultant solution and 10 ml of a dispersion obtained by dispersing the activated particles in a M/8 aqueous solution of sodium hydrogen carbonate with the polymer content adjusted to 1%, were mixed and stirred at room temperature for 4 hours. Next, the particles were centrifuged, washed with a M/8 aqueous solution of sodium hydrogen carbonate and thereafter dispersed in 20 ml of a 1% aqueous solution of ethanolamine (pH 10.0). The particles were stirred at room temperature for 3 minutes, centrifuged and washed with distilled water, then further washed with PBS 3 times and thereafter dispersed in 4 ml of PBS added with 1% of BSA to make the polymer content 5%. The so prepared dispersion of the particles immobilizing human IgG and a PBS solution of an IgG fraction of anti-human IgG antiserum (rabbit) were mixed on a microplate in the same manner as in Example 2 and a sedimentation pattern was visually observed. Agglutination was observed when the concentration of anti-human IgG antibody was not less than 1 μg/ml.

EXAMPLE 8

Glycidyl methacrylate, glycidyl acrylate, 2-hydroxyethyl methacrylate, 2-hydroxyethyl acrylate and ethyleneglycol dimethacrylate were mixed at a molar ratio of 30:25:20:20:5. 25 parts of this mixture of monomers was dissolved in 75 parts of n-propyl acetate, to the resultant solution was added 0.13 part of 2,2'-azobis (2,4-dimethyl-4-methoxyvaleronitrile) and the mixture was polymerized. The polymerization was carried out by allowing the solution to stand without agitation in a nitrogen gas atmosphere for 2 hours. The polymerization mixture was treated in the same manner as in Example 1 to obtain 8.4 parts of fine polymer particles. Further, hydrolysis by diluted sulfuric acid and amination by a treatment with ethylenediamine were carried out in the same manner as in Example 2. On the obtained aminated particles, human IgG was immobilized in the same manner as in Example 2. When the activity of the obtained particles immobilizing human IgG was verified in the same manner as in Example 2, it was possible to detect anti-human IgG antibody having a concentration of not less than 10 ng/ml by agglutination.

EXAMPLE 9

Example 1 was repeated except that an IgG fraction of anti-mouse IgG antiserum (goat) was used instead of the IgG fraction of anti-human IgG antiserum (rabbit) used in Example 1 to immobilize anti-mouse IgG antibody on the fine carrier particles. By the so prepared fine particles immobilizing anti-mouse IgG antibody, mouse spleen cells having IgG on the cell surfaces were labeled as follows. The spleen of an inbred mouse (male) 3 months of age was taken. While the cells were being cooled with ice, they were ground down in a physiological saline solution (isotonic sodium chloride solution), pipetted and then transferred to a test tube. This test tube was allowed to stand erect for 5 minutes and free cells only were sucked up by a Pasteur pipette and filtered with nylon gauze. The filtrate containing floating cells was subjected to centrifugal sedimentation at 4° C. and 800 r.p.m. for 5 minutes and further subjected to a similar centrifugal sedimentation in Eagle MEM culture medium, washed and thereafter the cells were dispersed at a ratio of $3 \times 10^6$/ml in Eagle MEM culture medium. The particles immobilizing anti-mouse IgG antibody were dispersed in PBS containing 1% of BSA at a ratio of $10^9$/ml. 0.2 ml of the dispersion of the cells and 0.2 ml of the dispersion of the particles immobilizing anti-mouse IgG antibody were mixed and incubated at 30° C. for 15 minutes, then centrifuged at 160 g for 1 minute. The sedimented cells and particles were mildly dispersed again. One drop of the resultant dispersion was taken and mixed with one drop of a solution of toluidene blue O on a slide glass. A unit wherein more than 3 polymer particles adhered to one cell was counted as one rosette under an optical microscope. The rosette-forming ratio of the mouse spleen cells was 20%. For comparison, when the similar experiment was carried out on mouse thymus cells, the rosette-forming ratio of such cells turned out to be only 2%.

EXAMPLE 10

Example 9 was repeated except that anti-mouse IgM antiserum (goat) was used, instead of the IgG fraction of anti-mouse IgG antiserum (goat) used in Example 9 to immobilize anti-mouse IgM antibody on the fine particulate carrier. With these fine particles, the mouse spleen cells having IgM on their surfaces were labeled in the same manner as in Example 9. As a result, the rosette-forming ratio of the mouse spleen cells was 22%. For comparison, as a result of carrying out a similar experiment with the mouse thymus cells, the rosette-forming ratio was 1%.

EXAMPLE 11

Thirteen mg of human γ-globulin was dissolved in 2 ml of physiological saline solution (isotonic sodium chloride solution), heated at 63° C. for 30 minutes, subjected to centrifugal sedimentation at 10,000 g for 30 minutes and the supernatant was skimmed. By high performance liquid chromatography, the ratio of monmeric human γ-globulin to aggregated human γ-globulin (hereinafter referred to as AHG) was determined to be 1:1 (a peak area ratio). This mixture was used for immobilization as crude AHG. As a carrier, fine aminated polymer particles prepared in the same manner as in Example 3 were similarly treated with glutaraldehyde and then used. A PBS solution containing 2 mg/ml of AHG and 10 mg/ml of BSA and the same volume of a PBS dispersion containing 1% of a carrier polymer similarly treated with glutaraldehyde were mixed. After stirring the mixed solution at 30° C. for 2 hours, it was subjected to centrifugal sedimentation. The fine particles precipitated as a result were washed with distilled water and dispersed again in PBS added with 1% of BSA and 0.02% of sodium azide to adjust the polymer content to 2.5%. On a slide glass, 10 μl of the so prepared dispersion of the fine particles immobilizing AHG was mixed with the same volume of control positive and negative serum of a reagent for detecting rheumatoid elements factor, "RA(KW)" (available commercially from Nippon Toketsu Kanso, Inc. of Japan). After about 1 minute, remarkable agglutination by the positive serum was observed; however, agglutination by the negative serum was not observed.

EXAMPLE 12

Fine aminated polymer particles were prepared in the same manner as in Example 1, treated with glutaraldehyde and dispersed in PBS at a concentration of 1%. Separately, protein A was dissolved in PBS at a concentration of 1 mg/ml. These were mixed at a ratio of 1:1 by volume and the resultant mixed dispersion was stirred at 30° C. for 2 hours. After completion of the reaction, the particles were centrifuged, washed with distilled water and dispersed in Veronal buffer saline solution (hereinafter referred to as VBS) at a concentration of 2.5%. The term "VBS" means a buffer aqueous solution obtained by dissolving 0.824 g of Veronal sodium salt, 8.5 g of sodium chloride, and 0.2 g of sodium azide in 1 liter of water and adjusting the pH to 8.0 with hydrochloric acid. When 10 μl each of a solution of diluted AHG prepared in the same manner as in Example 10 with VBS and a dispersion of fine particles immobilizing protein A were mixed on a slide glass, agglutination was observed at a concentration of AHG of not less than 30 μg/ml. In contrast thereto, where AHG dissolved in human serum was diluted 2 times with VBS, agglutination was not observed even when the concentration of AHG was 130 μg/ml. This result is thought to have occurred because IgG contained at a high concentration in human serum bonded to protein A immobilized on the surfaces of the fine particles, thus inhibiting agglutination of the fine particles immobilizing protein A by AHG.

EXAMPLE 13

In 45 ml of a 10% aqueous solution of ammonia, 0.3 g of fine particles, obtained by carrying out polymerization in the same manner as in Example 6, were dispersed and the resulting mixture was stirred at 40° C. for 1 hour. After washing the fine particles with distilled water 4 times, the particles were dispersed in a mixed solution of 15 ml of 0.5% dilute sulfuric acid and 15 ml of acetone and the mixed dispersion was stirred at 30° C. for 10 days. The fine particles were washed with distilled water 3 times, with a M/10 solution of sodium carbonate twice and again with distilled water 3 times. Next, 0.1 g of the fine particles was dispersed in 20 ml of distilled water, to which was added 3 ml of a 25% aqueous solution of glutaraldehyde and the resulting mixture was stirred at 30° C. for 1 hour. After washing these fine particles with distilled water 3 times and with PBS once, the fine particles were dispersed again in 1.5 ml of PBS.

One mg of an IgG fraction of anti-HCG antiserum (rabbit) containing 0.055 mg of the antibody was dissolved in 0.25 ml of PBS, the resultant solution was mixed with the dispersion of the fine particles treated with glutaraldehyde and the mixture was stirred at 30° C. for 16 hours. Next, the fine particles were washed with PBS 3 times and dispersed again in 10 ml of PBS added with 1% of BSA. Fifty μl each of the dispersion of the fine particles immobilizing anti-HCG antibody and an HCG/PBS solution having a predetermined concentration were mixed on a V-shaped microplate, allowed to stand still for 2 hours and thereafter the sedimentation patterns were visually observed. The results are shown in Table 5.

TABLE 5

| HCG concentration (IU/liter) | $10^4$ | $10^3$ | $10^2$ | 10 | 1 | 0.1 | 0 |
|---|---|---|---|---|---|---|---|
| Agglutination | +++ | +++ | +++ | ++ | + | ± | − |

Next, 25 μl of a solution obtained by diluting to 100 times an anti-HCG antiserum having an antibody concentration of 0.24 mg/ml and 25 μl of an HCG/PBS solution of concentrations twice as in Table 5 were mixed on a microplate and the mixture was incubated at 30° C. for 1 hour. Thereafter 50 μl of a dispersion of fine particles immobilizing anti-HCG antibody were added to the incubated mixture. The resultant mixture was allowed to stand still for 2 hours and the sedimentation was observed. Agglutination was not observed at the concentrations of HCG within the ranges of 0.1 IU/liter—$10^4$ IU/liter. Accordingly, agglutination in the experiment of Table 5 was caused by the reaction between the antigen and the antibody and the sensitivity for detecting HCG is 1 IU/liter.

What is claimed is:

1. A diagnostic reagent for immunological testing comprising
   (a) a particulate carrier composed of fine particles having an average diameter within the range of 0.03–10 μm, said carrier comprising a cross-linked polymer having a repeating unit represented by the general formula

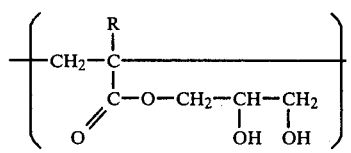

wherein R denotes hydrogen or a methyl group and (b) an immunochemical immobilized on said particulate carrier.

2. A diagnostic reagent for immunological testing according to claim 1, wherein said fine particles are comprised of a cross-linked polymer containing more than about 50 mol % of the repeating unit represented by the general formula and less than about 50 mol % of a copolymerizable monomer unit selected from the group consisting of 2-hydroxyethyl acrylate and 2-hydroxyethyl methacrylate.

3. A diagnostic reagent for immunological testing according to claim 1, wherein said immunochemicals are selected from the group consisting of Treponema pallidum antigen, human chorionic gonadotropin, anti-human chorionic gonadotropin antibody, anti-human IgG antibody, anti-human IgM antibody, aggregated human IgG and protein A.

4. A process for preparing diagnostic reagents for immunological tests which comprises polymerizing a mixture of addition polymerizable monomers containing more than about 50 mol % of glycidyl acrylate and glycidyl methacrylate in a medium in which said mixture of monomers is soluble but in which the polymer produced is not soluble, treating the fine particulate polymer precipitated with a hydrolyzing agent and immobilizing immunochemicals by covalent bonding on fine particles having an average diameter within the range of about 0.03-10 μm and consisting of the so-obtained cross-linked polymer having a repeating unit represented by the general formula

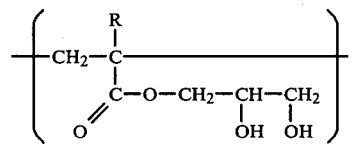

wherein R denotes hydrogen or a methyl group.

5. A process for preparing diagnostic reagents for immunological tests according to claim 4, wherein either before or after treating said fine particulate polymer with a hydrolyzing agent, said fine particulate polymer is treated with an aminating agent selected from the group consisting of ammonia, hydrazine and an organic amine having not less than 2 amino groups within the molecule, to thereby introduce an amino group into said fine particulate polymer and immunochemicals having an amino group are immobilized on said fine particulate cross-linked polymer containing an amino group using a compound having 2 or more functional groups bondable to amino groups within the molecule as a binder.

6. A process for preparing diagnostic reagents for immunological tests according to claim 4, wherein said mixture of addition polymerizable monomers contain up to about 30 mol % of an addition polymerizable monomer having a carboxyl group to thereby introduce a carboxyl group to said fine particulate cross-linked polymer having said repeating unit represented by the general formula [I], wherein an amide bond is caused to be produced from the amino group of said immunochemicals having an amino group and wherein the carboxyl group of said fine particulate cross-linked polymer immobilizes said immunochemicals onto said fine particulate cross-linked polymer.

7. A reagent useful in diagnostic immunological testing comprising (1) an immobilizing carrier including a cross-linked polymer having a repeating unit represented by the general formula

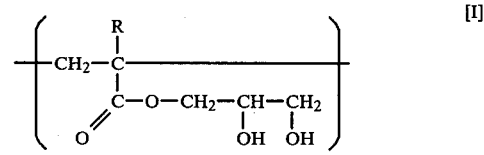

wherein R denotes hydrogen or a methyl group, and (2) an immunochemical, bonded to said carrier, selected from the group consisting of Treponema pallidum antigen, human chorionic gonadotropin, anti-human chorionic gonadotropin antibody, anti-human IgG antibody, anti-human IgM antibody, aggregated human IgG and protein A.

8. A process for producing a composition of matter useful in diagnostic immunological testing as an immobilizing carrier for immunochemicals comprising (1) polymerizing a mixture of addition polymerizable monomers containing more than 50 mol % of glycidyl acrylate and glycidyl methacrylate in a medium in which said mixture of monomers is soluble, but in which the polymer produced is not soluble, to produce a polymer, (2) treating said polymer with a hydrolyzing agent to produce a cross-linked polymer having a repeating unit represented by the general formula [I]

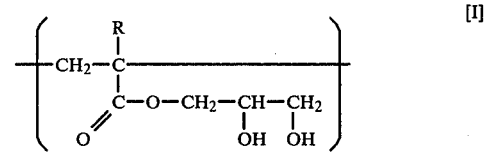

wherein R denotes hydrogen or a methyl group, (3) treating said polymer with an aminating agent selected from the group consisting of ammonia, hydrazine or an organic amine having 2 or more amino groups within the molecule, to add an amino group onto said polymer, and (4) immobilizing immunochemicals having an amino group on said polymer containing an amino group using a compound having 2 or more functional groups, bondable to amino groups within the molecule, as a binder.

* * * * *

UNITED STATES PATENT AND TRADEMARK OFFICE
CERTIFICATE OF CORRECTION

PATENT NO. : 4,418,152

DATED : November 29, 1983

INVENTOR(S) : Shuntaro Hosaka; Yasuo Murao and Yasuro Kawabata

It is certified that error appears in the above-identified patent and that said Letters Patent is hereby corrected as shown below:

Column 1, line 66, delete "euilibrium" and insert --equilibrium--.

Column 17, line 20, after "formula" insert --[1]--.

Signed and Sealed this

Nineteenth Day of June 1984

[SEAL]

Attest:

Attesting Officer

GERALD J. MOSSINGHOFF

Commissioner of Patents and Trademarks